(12) United States Patent
Bacon (10) Patent No.: US 9,114,926 B2
(45) Date of Patent: Aug. 25, 2015

(54) DISPENSING CONTAINER

(75) Inventor: Raymond J. Bacon, Petersfield (GB)

(73) Assignee: TRIG1 LIMITED, Waterlooville (GB)

( * ) Notice: Subject to any disclaimer, the term of this patent is extended or adjusted under 35 U.S.C. 154(b) by 101 days.

(21) Appl. No.: 13/576,751

(22) PCT Filed: Feb. 1, 2011

(86) PCT No.: PCT/GB2011/000126
§ 371 (c)(1),
(2), (4) Date: Sep. 12, 2012

(87) PCT Pub. No.: WO2011/095761
PCT Pub. Date: Aug. 11, 2011

(65) Prior Publication Data
US 2013/0001258 A1 Jan. 3, 2013

(30) Foreign Application Priority Data
Feb. 3, 2010 (GB) .................................. 1001762.2

(51) Int. Cl.
*B65D 83/38* (2006.01)
*A61M 15/00* (2006.01)
(52) U.S. Cl.
CPC .............. *B65D 83/38* (2013.01); *A61M 15/009* (2013.01); *A61M 2205/3389* (2013.01); *A61M 2205/583* (2013.01); *B65D 2203/045* (2013.01)
(58) Field of Classification Search
CPC .. G01F 23/00; B65D 2203/045; B65D 83/38; A61M 15/009; A61M 2205/583; A61M 2205/3389

USPC ................... 222/41, 463, 402.1, 51, 23, 154; 73/309; 248/130, 133; 340/612; 116/200, 228, 227, 215; 220/631, 669
See application file for complete search history.

(56) References Cited

U.S. PATENT DOCUMENTS

| 3,505,870 | A | * | 4/1970 | Smylie | 73/323 |
| 3,885,698 | A | | 5/1975 | Lebel et al. | |
| 4,257,558 | A | * | 3/1981 | Mason, Jr. | 239/57 |
| 5,579,759 | A | * | 12/1996 | Gantz | 128/200.24 |
| 5,785,048 | A | | 7/1998 | Koerner | |
| 5,860,552 | A | * | 1/1999 | Culhane et al. | 220/212 |
| 6,581,539 | B1 | | 6/2003 | Rasor | |
| 7,168,433 | B2 | * | 1/2007 | De LaForcade | 132/116 |

FOREIGN PATENT DOCUMENTS

| FR | 2 736 331 | 1/1997 |
| GB | 2 348 676 | 10/2000 |
| WO | WO 98/07459 | 2/1998 |

OTHER PUBLICATIONS

International Search Report for PCT/GB2011/000126, mailed Jun. 21, 2011, (Daintith, Edward).

* cited by examiner

*Primary Examiner* — Kevin P Shaver
*Assistant Examiner* — Robert Nichols, II
(74) *Attorney, Agent, or Firm* — Nixon & Vanderhye P.C.

(57) ABSTRACT

A container (101) has a constant wall thickness vessel (102) with a valve (103) crimped on at a neck (104) in the vessel. The valve has a dispensing stem (105). The vessel is circularly cylindrical and formed with an groove (106) extending parallel with the length of the vessel, from a base (107) to the neck (104). When the container is lain on its sidewall (108), it will roll, changing its orientation, until the groove (106) is at the surface as shown in FIG. 7, with the groove in effect floating on the surface of the liquid, providing an indication of the actual quantity of content in the container.

9 Claims, 8 Drawing Sheets

DISPENSING CONTAINER

This application is the U.S. national phase of International Application No. PCT/GB2011/000126, filed 1 Feb. 2011, which designated the U.S. and claims priority to GB Application No. 1001762.2, filed 3 Feb. 2010, the entire contents of each of which are hereby incorporated by reference.

The present invention relates to a dispensing container.

In this specification the term "gravitational torque" is used and its meaning is, in respect of a pivot axis or fulcrum and a gravitational attraction acting through a centre of gravity, the product as torque of the gravitational attraction and the horizontal spacing of the pivot axis or fulcrum and the centre of gravity.

The terms "attitude" and "orientation" are also used in respect of the disposition of a container on a flat surface:
"Attitude" means the container's general disposition, in particular either of its stood-on-end attitude or its lain-on-its-side attitude;
"Orientation" means its angle within its attitude, in particular its angle to the vertical or angle of tilt[1] when in the stood-on-end attitude or the angle to which it rolls when in the lain-on-its-side attitude.

[1] c.f. The leaning Tower of Pisa.

The term "cylinder" is used herein in its mathematical meaning, namely: "A surface generated by a line which moves parallel to a fixed line so as to cut a fixed plane curve".[2]

[2] Chambers Dictionary of Science and Technology

A cylinder can be "infectionless" when the plane curve has no changes in the sign of its curvature, in other words where it is convex throughout its extent. Alternatively, it can be "inflected" when the curve includes a change in curvature sign, i.e. it includes a concavity. The most common cylinder is a "right circular cylinder" in which the curve is a circle and the fixed line is at right angles to the plane of the circle. Purely by way of illustration, if the curve is an ellipse, the cylinder is an elliptical cylinder.

Metered dose inhalers use a container of the following type, "the type defined", namely a pressurised liquid dispensing container comprising:
a valve for dispensing the liquid from the container; and
a vessel containing the liquid under pressure, the vessel having:
a valve end to which the valve is attached,
a sidewall having an at least partially cylindrical shape and an end wall,
the vessel defining:
an inflectionless cylindrical envelope,
whose cross-section is the cross-section of the vessel at the sidewall and
whose length is the length of the vessel between the valve end and the end wall.

A problem with this type of pressurised liquid dispensing container is that normally the vessel is made of impact extruded aluminium or rolled and welded sheet steel; these materials are opaque. It is not possible to see the quantity of liquid in the container; nor can it be readily assessed by normal handling, feel nor sound.

Nevertheless there is a requirement for such assessment, particularly in the medical field.

The object of the present invention is to provide an improved pressurised liquid dispensing container.

According to the invention there is provided a pressurised liquid dispensing container of the type defined, the container having within the inflectionless cylindrical envelope:
a formation of the vessel or a discrete element in the vessel which causes the centre of gravity of liquid contents of the container to be positioned differently, at least in one attitude of the container, from its notional position, in the absence of the formation-or-element, the formation-or-element also being such that:
when the container is in the one attitude and is at least substantially full of liquid contents, the centre of gravity of the liquid biases the container to one orientation thereof in the one attitude and
when the container is at least empty or nearly so, the centre of gravity of the container per se, in the absence or near absence of liquid contents, biases the container to another orientation thereof in the one attitude or biases it into another attitude.

Normally the cylindrical envelope will be a right circular cylindrical envelope, although for special purposes, other cylindrical envelopes can be envisaged.

Further the formation where provided within the envelope can be an inflection of the sidewall within the inflectionless cylindrical envelope. In which case sidewall may have an inflected cylindrical shape along at least part of its length. However in certain embodiments the formation is a shaped truncation of the vessel at its end wall, with the furthest extent of the end wall defining the end of the cylindrical envelope.

Normally the valve is of the type in which depression of a central stem of the container releases a metered dose. However this invention is not restricted to metered dose containers, but includes container of the type in which a continuous stream of liquid can be dispensed from the valve.

It is envisaged that the containers of the invention can have the formation-or-element arranged for estimation of their contents either when in the stood-on-end attitude or when in the lain-on-side attitude. We find the respective descriptions "bi-stable" and "roll-stable" to be useful. However, these are used hereinbelow only in respect of the specific embodiments, not least because we envisage that the stood-on-end attitude arrangement can in fact have more than two stable states.

In the stood-on-end attitude alternative:
the formation-or-element is a formation at the end wall end of the vessel providing:
a support area for stable support of the container when full, the formation providing the support area such that:
the centre of gravity of the container per se is without the support area, that is vertically outside the support area when the latter is horizontal and defining an outside point in a plane of the support area,
the centre of gravity of the liquid contents, when the container is full, is within, that is vertically within, the support area, when the latter is horizontal, and defining an inside point in a plane of the support area,
a line joining the outside point and the inside point intersects a perimeter of the support area at a fulcrum point and
the gravitational torque of the centre of gravity of the full liquid contents about the fulcrum point exceeds the gravitational torque of the centre of gravity of the container per se,
the arrangement being such that as the liquid is dispensed standing of the container in its stood-on-end attitude, the container remains stable whilst the gravitational torque of the liquid exceeds that of the container, but the container loses its stood-on-end stability when the gravitational torque of the liquid ceases to exceed that of the container.

In a simple embodiment of this alternative, the end wall of the vessel is angled with respect to a normal plane across the circular cylindrical envelope such that when the container is stood on end, it is tilted. The angle of tilt is such that the empty container tilts further. This angle may be 15° to 18°. It is more likely to between 18° and 25° or more, but is unlikely to be 30°.

Under 14°, the container is unlikely to fall over when empty, but can be induced to do so by addition of weight to the fulcrum side of the container.

The end wall can be plain at its angle, either flat or more likely indented; in either case the fulcrum point will be point of the end closest to the valve end of the vessel. Alternatively, the end wall can be ridged, both for grip and to provide a clearly defined fulcrum axis.

In another embodiment, the end of the wall is not angled with respect to the normal plane, but the end wall is formed with a fulcrum close to the central axis of the cylinder and a support, whereby the container can stand up right when full and stood on end. The end wall is formed with a punt between the fulcrum and the support, whereby when little liquid contents remains in the container, it is directed to occupy space in the vessel outside the fulcrum and cause the container to tip about the fulcrum.

Preferably the centre of gravity of the container per se is outside the fulcrum. Conveniently this can be arranged by adding weight to this side of the container. Alternatively the sidewall of the vessel at the end wall can be indented in the region of the support. This can have the effect of displacing the centre of gravity of the container per se eccentrically outside the fulcrum. The indent can also replace the punt. The centre of gravity can also be displaced be arranging the valve eccentrically of the cylinder of the vessel.

In an embodiment combining features of the above two embodiments, the fulcrum and the support tilt the container with its higher centre of gravity to fall outside the fulcrum, whereby it falls over when empty, yet the tilting is insufficient to cause the centre of gravity of the contained liquid to fall outside the fulcrum at least until the level of the punt is reached.

In either this or the preceding embodiment, the end wall outside the fulcrum can be formed to restrain the container from falling over completely from its stood-on-end attitude.

In the laid-on-side attitude alternative:
the formation-or-element is buoyant with respect to the contained liquid and is arranged to float on the liquid when the container is free to roll on its side and
the centre of gravity of the container per se (without contained liquid) is eccentric, whereby the container rolls to a stable position with the buoyant formation floating on the liquid,
the arrangement being such that the position to which the container rolls indicates the level of the liquid in the container.

Whilst the buoyant formation-or-element must displace some liquid and hence displaces the centre of gravity of the contained liquid from its position in absence of the formation-or-element, it should be noted that the displacement is likely to be small. Further the degree of eccentricity of the centre of gravity is equally likely to be small in that it counters the small displacement of the centre of gravity of the contained liquid.

Preferably, where the buoyant formation-or-element is a formation it is an inflection in the sidewall of the vessel. Conveniently it is formed such as to cause the centre of gravity to be eccentric. For instance, where the formation is a constant wall thickness indent, the indent has a longer extent than the equivalent piece of vessel wall on the opposite side of the vessel. Thus the indented formation biases the centre of gravity eccentrically towards itself.

Alternatively, if the formation is formed by stretching a piece of the wall, its effect on the centre of gravity, due to inwards movement of material, will be to bias the centre of gravity away from itself. In this situation, additional mass may be added, either internally of the vessel or externally.

Conveniently the indent extends from the end wall to the valve end of the vessel, whereby it acts as a wall displacing liquid in front of itself and giving a readily appreciable indication of the level of the liquid in the container.

Where the formation-or-element is an added element, conveniently attached to the valve or at least attached in the container by means of the valve attachment, which is otherwise conventional, the element will normally provide both the buoyancy and the eccentricity of the container's centre of gravity.

To help understanding of the invention, various specific embodiments thereof will now be described by way of example and with reference to the accompanying drawings, in which.

BI-STABLE EMBODIMENTS

Figure 1:
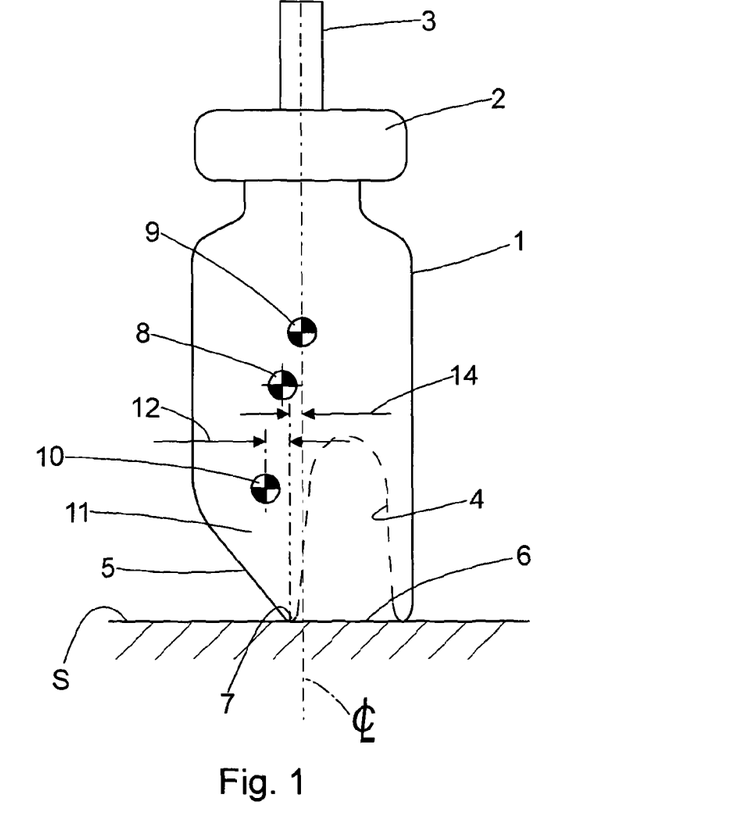
FIG. 1 is a side view of a first, bi-s table container in accordance with the invention.
Figure 2:
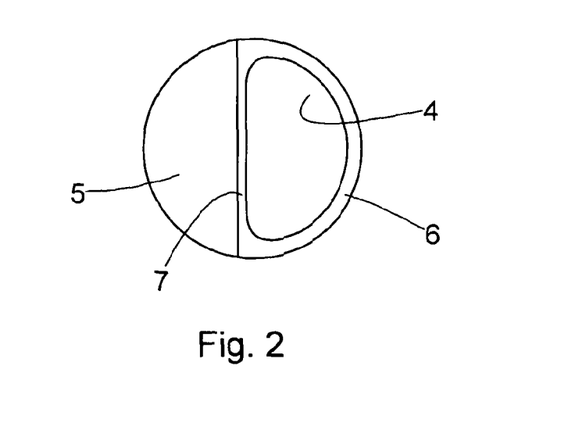
FIG. 2 is an underneath view of the source of FIG. 1.

Referring first to FIGS. 1 and 2, a pressurised medicament dispensing container is a source of medicament comprising a light alloy pressed body 1, a crimped on cap 2, a dispensing spout 3 and a conventional metered dose dispensing valve within the cap and not shown as such.

The end wall of the container remote from the cap is formed with a deep eccentric punt 4 and a chamfer 5, defining, with a rim 6 between the sidewall of the container and the punt, a fulcrum 7. The fulcrum is such that with the container stood on a flat surface S, pushing horizontally on the spout from the punt side will tip the container over once the righting moment of the weight of the contents of the container is overcome. The centre of gravity 9 of the contents above the punt is to the punt side of the fulcrum. The centre of gravity 8 of the container is just on the side of the fulcrum opposite from the punt.

It will be noted that the portion of the contents below the top of the punt has a centre of gravity 10 on the other side of the fulcrum. Taking account of the masses centred at the centres 8,9,10 and the relative positions of these centres of gravity with respect to the fulcrum, albeit with the centre of gravity 9 perhaps lower on account of use than as shown in FIG. 1, transition to instability, i.e. the gravitation torque of the contents level with the punt and of the container per se overcoming the gravitational torque of the contents above the punt, occurs with a small amount of the contents still remains above the punt; whereby standing of the source on end to test its contents with the space 11 to the side of the punt not quite full or indeed empty still causes instability if the test is carried out after reaching of the state where the contents extends above the punt to just a small extent.

Thus removal of the source from an inhaler or other applicator and its placing up-ended on a flat surface will indicate whether it has a useful amount of content of medicament and its propellant left inside or not. If it does the weight of the contents acting to the punt side of the fulcrum keeps the container upright, supported on the fulcrum and the stability support in the form of the rim 6. If not, i.e. if the container is empty or close to empty, the weight of the contents opposite the punt at a greater moment arm 12 is not counter-balanced by the greater weight of the contents above the punt albeit at a lesser moment arm 14. The container will not stand upright and it will fall over indicating that the container is empty or nearly empty.

Figure 3:
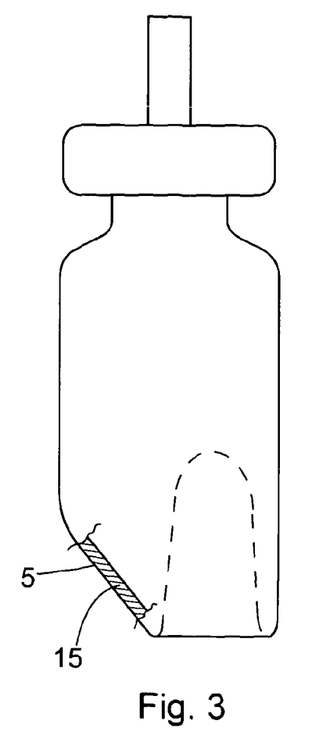
FIG. 3 is a partially sectioned view similar to FIG. 1.

Turning now to FIG. 3, the variant there shown has a thick portion 15 of the chamfer wall 5, which biases the centre of gravity of the container away from the punt.

Figure 4:
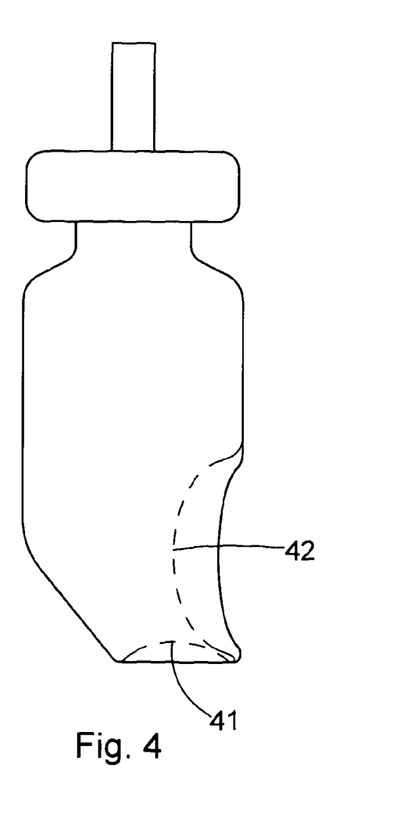
FIG. 4 is a side view similar to FIG. 1 of a source including a variant.

The container just described is envisaged to be able to be made by deep pressing. An alternative container is shown in FIG. 4. This has a shallower punt 41 and a depression 42 in the sidewall of the container. The depression biases the centre of gravity of the container to the opposite side of the fulcrum. This container is envisaged to be able to be made by hydroforming. The same effect can be envisaged to be obtainable by moving the valve and spout by a small amount, i.e. not enough to affect operation of the container in a conventional inhaler/dispenser, but enough to bias the centre of gravity of the container.

Figure 5:
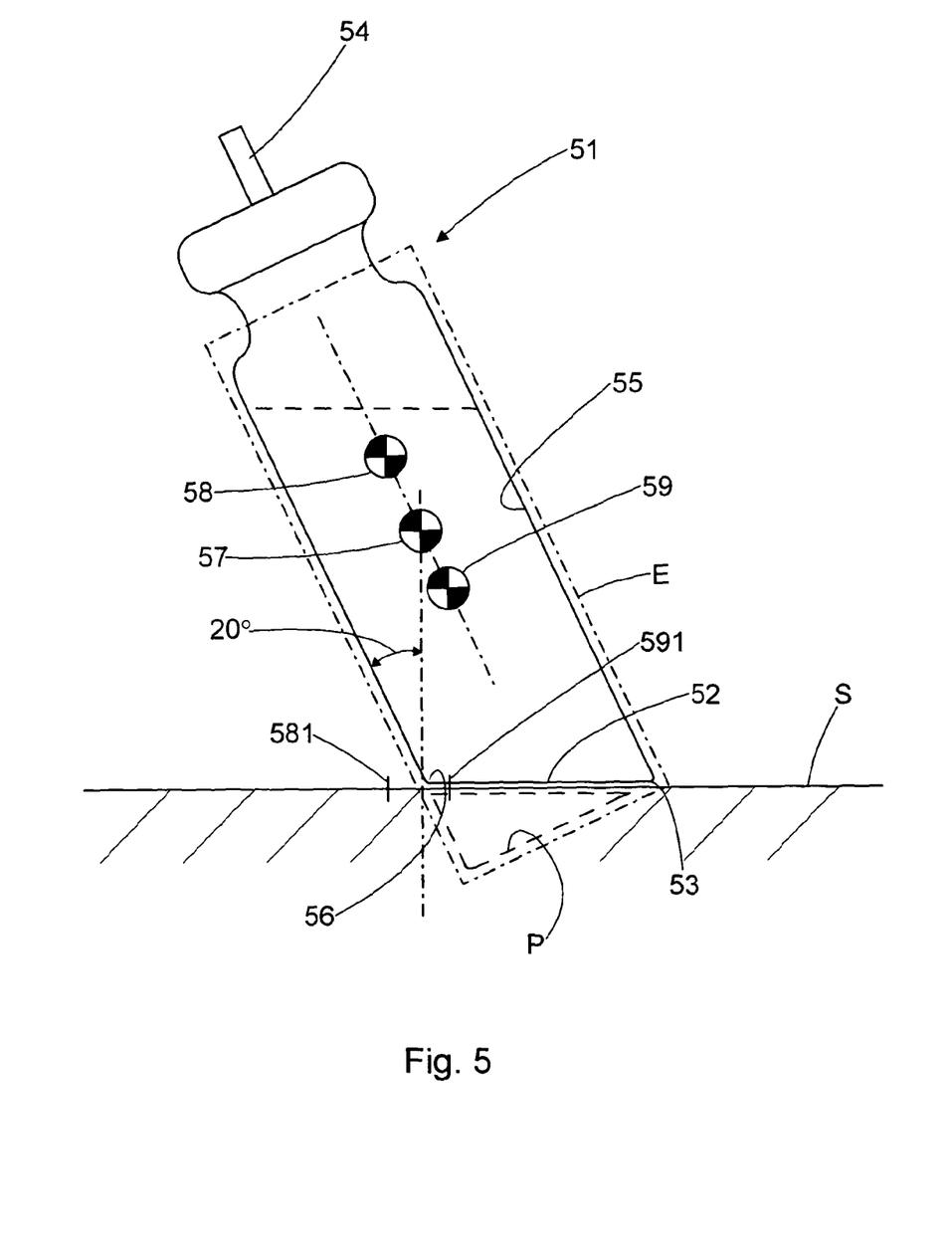
FIG. 5 a side view of another bi-s table container in accordance with the invention.

The embodiment of FIG. 5 is simpler as regards the formation of the vessel and its difference from a conventional pressurised liquid dispensing container. In terms of the scantlings of a container of the same length and diameter as that of the container of FIG. 5, shown by the envelope E, the container 51 has an angled end wall 52, whose furthest extent 53 from the dispensing spout 54 is as far as the end of the envelope, leaving a triangular end portion P absent from the container 51.

When the container is stood on a level surface S, it has an angle of tilt of 20° as drawn. The end wall 52 is plain and elliptical in its plane, the impact extruded vessel 55 of the container being right, circular cylindrical. One elliptical extreme of the end wall is at the extent 53 and the other is a fulcrum point 56. (It should be noted that although fulcra are normally wide to provide a pivot axis, the width between the sides of the ellipse provide lateral stability whereby it is the fulcrum point which provides stability against tipping). The length of the vessel, its diameter and the angle of tilt are all such that the centre of gravity 57 of the vessel as such is vertically, or nearly so, above the fulcrum point. The vessel carries not only the spout 54, but the associated valve etc. which are conventional and not shown. The result is that the centre of gravity 58 of container as such is outside the fulcrum. The liquid contents 59 do not reach up to the top of the vessel, even when full. To a first approximation the centre of gravity of the vessel and contents extending to the full height of the vessel are close if not coincident. Therefore the centre of gravity 59 of the contents falls inside the fulcrum and the design of the container can be fine tuned to arrange that the container is stable when full.

In more detail the centres 58,59 of gravity intersect the plane of the end wall when the latter is horizontal at points 581,591. The line between the points intersects the perimeter of the end wall at the fulcrum point 56. The gravitational torques of the two centres of gravity, that is to say the product of the masses notionally at the centres and their moment arms from the points 581,591 to the fulcrum point, must be such that the gravitational torque of the contents is larger for stability when the container is full. When some of the contents has been used, the gravitational torque of the contents increases as less of the contents is outside the fulcrum. In practice, the mass of the contents is decreasing but the moment arm is increasing. This effect continues (with successive estimations of content as liquid is dispensed) until the liquid is all inside the fulcrum. Its gravitational torque then decreases until, when there is none left, the over-turning torque of the container per se causes the container to fall over from its stood-on-end (albeit tilting) attitude to its lain-on-side attitude. The point of actual tipping will be when a small amount of liquid is left. Thus if the container stands on end the user knows that there is a quantity left with a reserve; if the container won't stand on end, the reserve is already being consumed.

Although the end wall is described above as flat in practice is likely to be slightly dished in to avoid it bowing out under the pressure of the contents as is conventional.

Roll-Stable Embodiments

Figure 6:
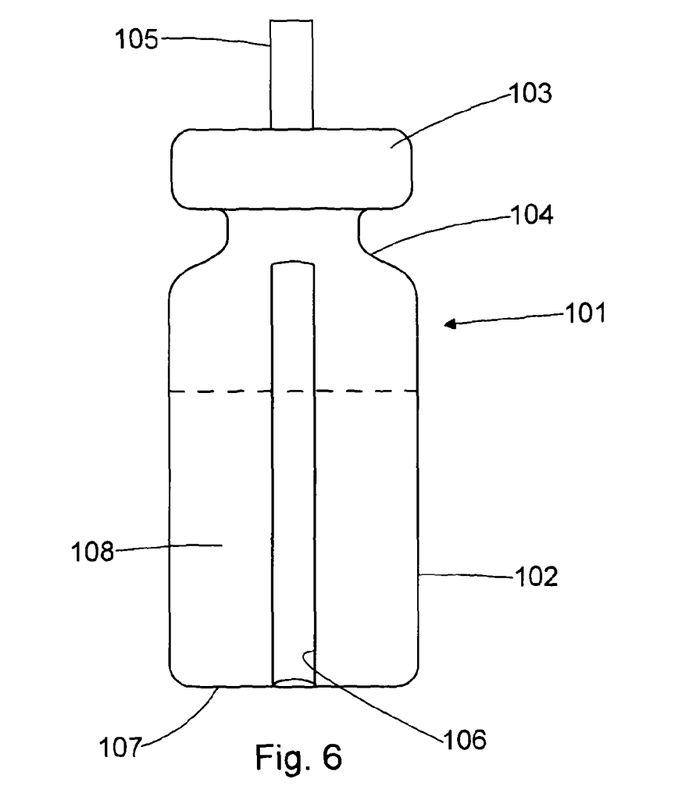
FIG. 6 is a side view of a roll-stable container in accordance with the invention.
Figure 7:
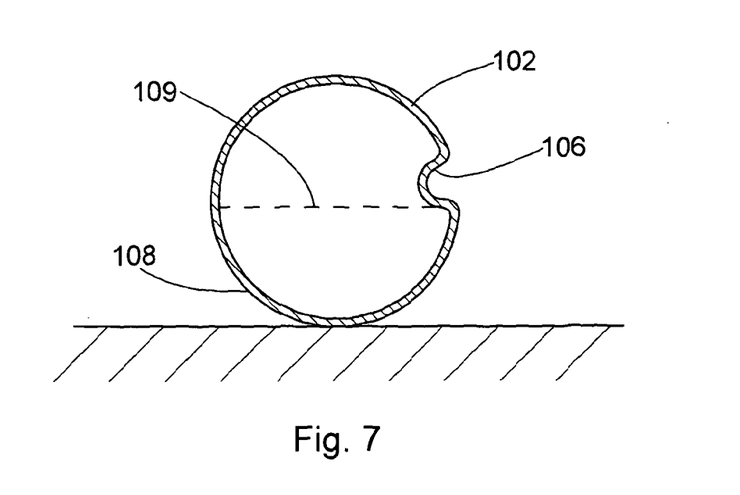
FIG. 7 is a cross-section view of the container with its buoyant formation in the surface of the contained liquid.

Referring to the drawings, in FIGS. 6 and 7, the roll-stable pressurised liquid dispensing container 101 thereshown has a constant wall thickness vessel 102 with a valve 103 crimped on at a neck 104 in the vessel. The valve has a dispensing stem 105. The vessel is circularly cylindrical and formed with an groove 106 with its circular cylindrical envelope, extending parallel with the length of the vessel, from a base 107 to the neck 104, giving it an inflected circular cylindrical sidewall. The arrangement is such that when the container is in the attitude of being lain on its sidewall 108, in which the groove is, if the groove is initially beneath the surface 109 of the liquid in the container, the latter will roll, changing its orientation, until the groove 106 is at the surface as shown in FIG. 7, with the groove in effect floating on the surface of the liquid. If the groove is initially above the liquid, since it biases the centre of gravity of the vessel and the container towards itself, being of constant wall thickness, the container will again roll until the groove is floating on the surface of the liquid. Thus the extent of fullness of the container can be determined by where the groove comes to rest. When the liquid level is low, the groove extending from end to end of the vessel, provides a particularly accurate indication of content, since liquid cannot flow behind it. It should be noted that whilst the embodiments of FIGS. 1 to 5 can be tested in a binary manner as to whether there is enough content for the time being or there is not; the embodiment of FIGS. 6 and 7 provides an analogue indication of the actual quantity of content in the container.

Figure 8:
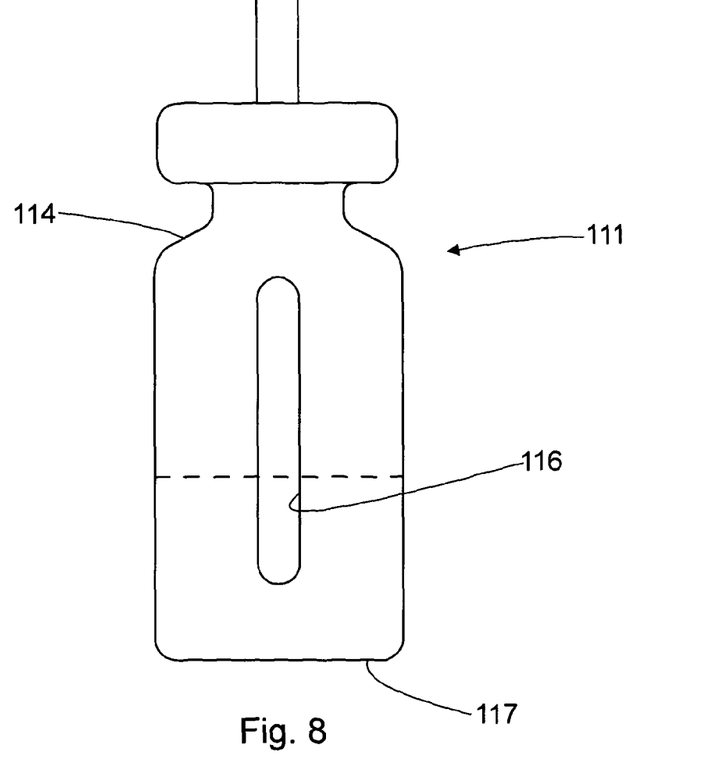
FIG. 8 is a side view a second roll-stable container in accordance with the invention.
Figure 9:
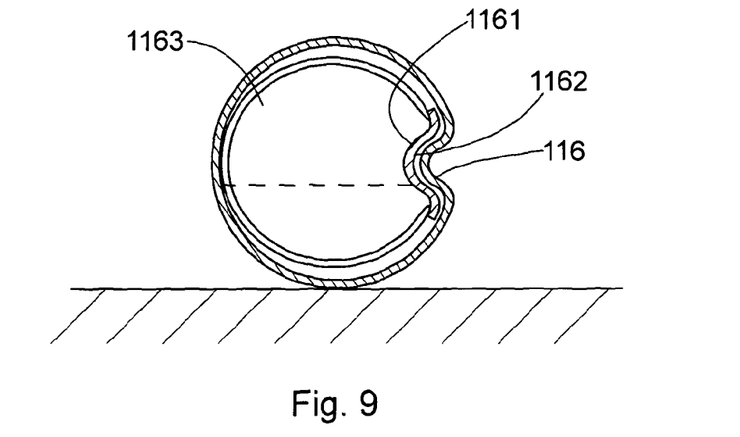
FIG. 9 is a cross-section view of the container of FIG. 3 with its buoyant formation in the surface of the contained liquid.

Referring on to FIGS. 8 and 9, this container 111 has a groove 116 which stops short at its ends of the neck 114 and base 117. The groove is formed as an indent by locally stretching the material of the wall. Thus the material at the groove does not have enough mass to bias the groove to float on the liquid if it is initially above the liquid level. For this, an inner strip 1161 having its groove 1162 is added. It is envisaged that this can be carried into the vessel with a die into which the groove is stamped, uniting the grooves. Alternatively inner strip can be fitted after the groove 116 has been formed and held in place by a spring 1163. This container rolls to indicate the liquid level in like manner to that of FIGS. 6 & 7.

Figure 10:
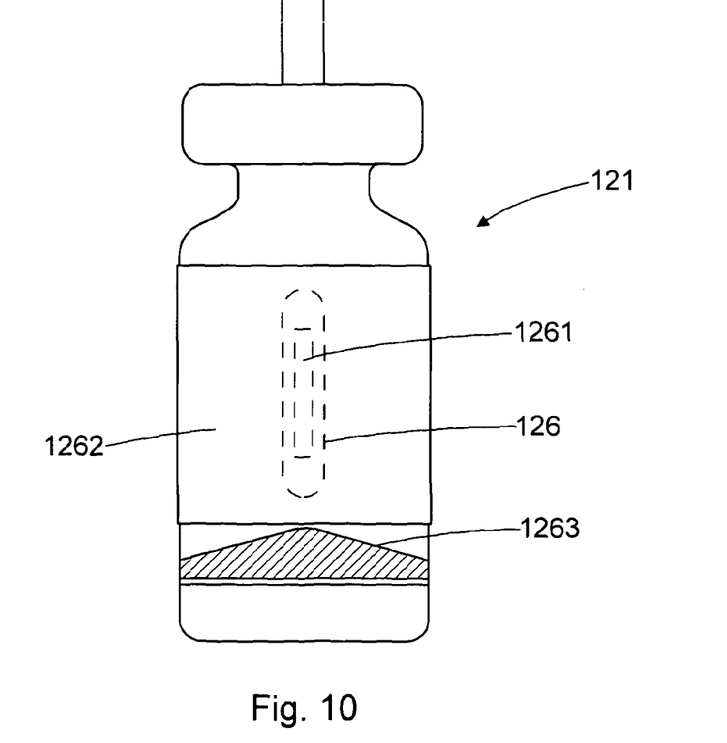
FIG. 10 is a side view a third roll-stable container in accordance with the invention.
Figure 11:
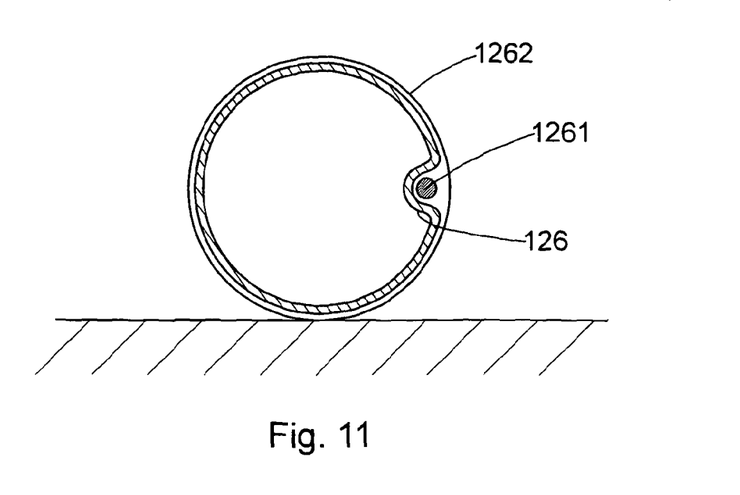
FIG. 11 is a cross-section view of the container of FIG. 5 with its buoyant formation in the surface of the contained liquid.

The container 121 of FIGS. 10 and 11 has a groove 126 which carries an external weight 1261. This can be held in place by friction, adhesive or indeed by an external label 1262. The latter can be formed with indicia 1263 indicating the extent to which the container is full or empty, in accordance with the portion of the indicia which comes to rest upper-most. Naturally the external weight, nor indeed any added internal weight, must not be too heavy as to overcome the buoyant effect of the formation and cause the container always to roll to the empty orientation.

Figure 12:
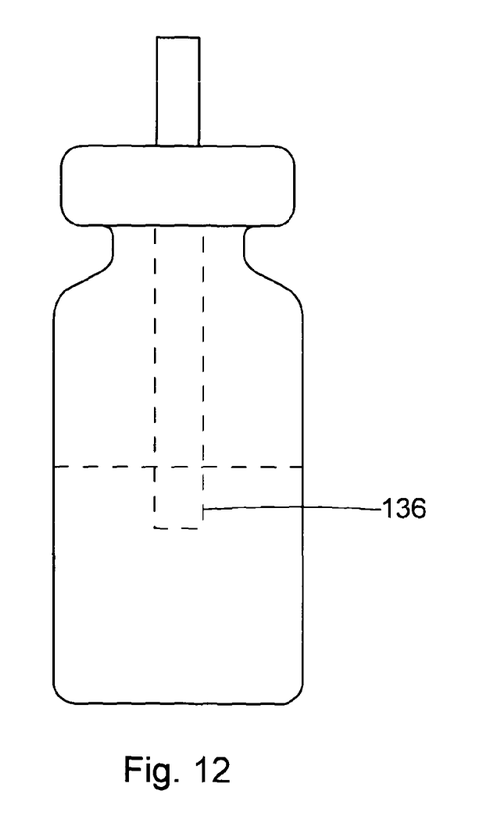
FIG. 12 is a side view a fourth roll-stable container in accordance with the invention.
Figure 13:
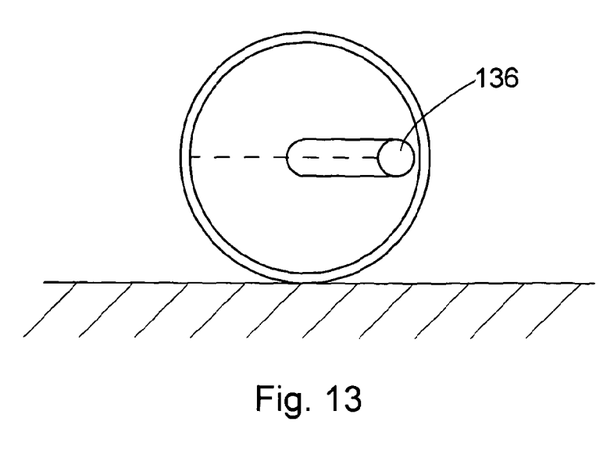
FIG. 13 is a cross-section view of the container of FIG. 7 with its buoyant formation in the surface of the contained liquid.

The embodiment of FIGS. 12 and 13 has an internal buoyancy element 136, which is independent of the wall of the vessel and is fast with the rest of the container via the crimped on valve. This element is clear of the sidewall, whereby when the content is low, the element 136 reaches its lowest position before the content is exhausted. This gives an advantageous indication of a reserve.

Figure 14:
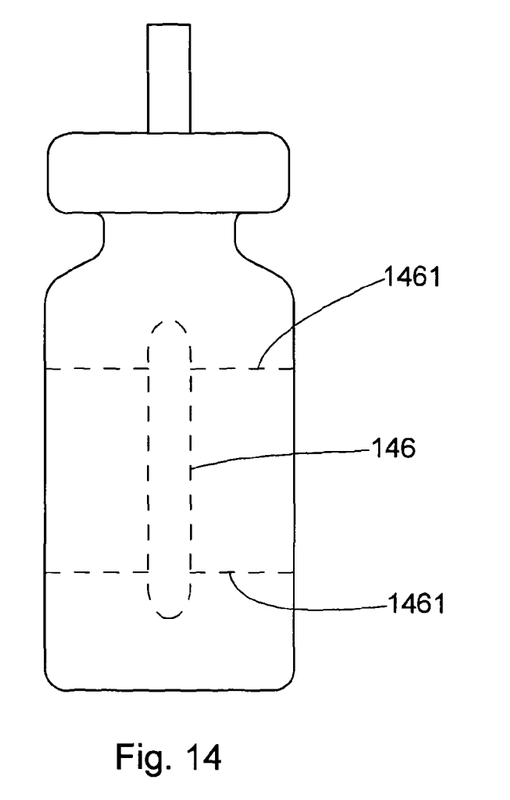
FIG. 14 is a side view a fifth roll-stable container in accordance with the invention.
Figure 15:
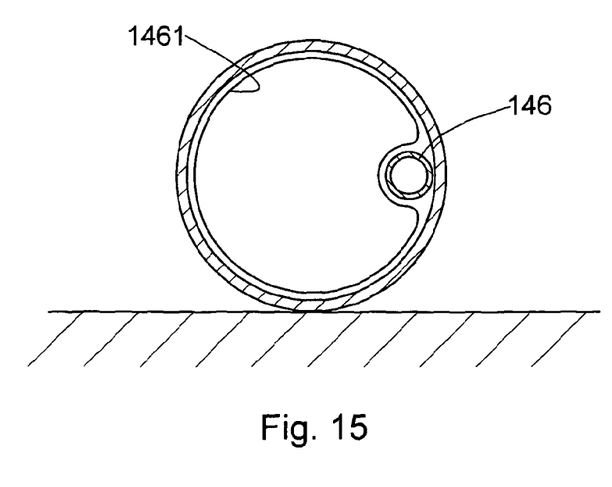
FIG. 15 is a cross-section view of the container of FIG. 9 with its buoyant formation in the surface of the contained liquid.

Again the embodiment of FIGS. 14 and 15 also has an internal buoyancy 146, in the form of a small buoyant tube, which is held in place against the side wall of the vessel by a spring 1461, in the manner of the inner strip 1161 and its spring 1163. In both these embodiments, there is no external indication of where the buoyant formation is. However external indicia, via a label or other wise, can be added either before the container is filled, by controlled manufacture, or after filling when the container will adopt its "full" position, with respect to which the indicia can be applied.

The invention is not intended to be restricted to the details of the above described embodiment. For instance, not only can the invention be used for metered dose medical inhalers, but it can also be used for general purpose aerosol dispensers. Further, it can be used for containers having metal vessels, in particular aluminium and steel vessels, as well as plastics materials vessels.

The invention claimed is:

1. A pressurised liquid dispensing container of the type defined, the container comprising a vessel for containing the liquid under pressure, the vessel defining an inflectionless cylindrical envelope; the container having within the inflectionless cylindrical envelope:
    a formation and/or a discrete element in the vessel which causes the centre of gravity of liquid contents of the container to be positioned differently when the container is in a lain-on-side attitude, the formation-or-element also being such that:
    when the side wall of the container is lain on a surface and the container is at least substantially full of liquid contents, the centre of gravity of the liquid biases the container to roll towards one orientation thereof and
    when the container is at least empty or nearly so, the centre of gravity of the container, in the absence or near absence of liquid contents, biases the container to roll towards another orientation thereof.

2. A container as claimed in claim 1, wherein the formation where provided within the envelope is an inflection of the sidewall within the cylindrical envelope.

3. A container as claimed in claim 2, wherein the sidewall has an inflected cylindrical shape along at least part of its length.

4. A container as claimed in claim 2, wherein the formation is a shaped truncation of the vessel at its end wall, with the furthest extent of the end wall defining the end of the cylindrical envelope.

5. A container as claimed in claim 1, wherein the valve is of the type in which depression of a central stem of the container releases a metered dose.

6. A container as claimed in claim 1, wherein the valve is of the type in which depression of a central stem of the container releases a continuous stream of liquid from the valve.

7. A container as claimed in claim 1, wherein:
    the formation-or-element is buoyant with respect to the contained liquid and is arranged to float on the liquid when the sidewall of the container is lain on a surface and
    the centre of gravity of the container without contained liquid is eccentric, whereby the container rolls to a stable position with the buoyant formation floating on the liquid,
    the arrangement being such that the position to which the container rolls indicates the level of the liquid in the container.

8. A container as claimed in claim 7, wherein the buoyant formation-or-element is an indent formed in the sidewall of the vessel.

9. A container as claimed in claim 8, wherein the buoyant formation-or-element is an indent formed such as to cause the centre of gravity of the container to be eccentric.

* * * * *